US00PP26317P2

(12) United States Plant Patent
Jack

(10) Patent No.: US PP26,317 P2
(45) Date of Patent: Jan. 19, 2016

(54) ***CHAMELAUCIUM* PLANT NAMED 'MOONLIGHT DELIGHT'**

(50) Latin Name: ***Chamelaucium* hybrid**
Varietal Denomination: Moonlight Delight

(71) Applicant: Brian Jack, Coorow (AU)

(72) Inventor: Brian Jack, Coorow (AU)

(73) Assignee: WAFEX PTY LTD, Perth (AU)

( * ) Notice: Subject to any disclaimer, the term of this patent is extended or adjusted under 35 U.S.C. 154(b) by 109 days.

(21) Appl. No.: 13/999,146

(22) Filed: Jan. 21, 2014

Related U.S. Application Data

(60) Provisional application No. 61/849,565, filed on Jan. 29, 2013.

(51) Int. Cl.
*A01H 5/00* (2006.01)

(52) U.S. Cl.
USPC ..... Plt./229

(58) Field of Classification Search
USPC ..... Plt./229
See application file for complete search history.

(56) References Cited

PUBLICATIONS

"Exciting Range of New Waxflower Varietes for the Middle East," Gulf Agriculture, Jul.-Aug. 2011, pp. 16-18.*

* cited by examiner

*Primary Examiner* — Susan McCormick Ewoldt
(74) *Attorney, Agent, or Firm* — Penny J. Aguirre

(57) ABSTRACT

A new cultivar of *Chamelaucium*, 'Moonlight Delight', that is characterized by its large clear white flowers with crimson centers, with the white color retained as the flower age, its red flower buds, its long harvest period as a cut flower, its flowers with overlapping petals, its calyxes with the free apex portion remaining mostly white, and its early blooming habit.

1 Drawing Sheet

Botanical classification: *Chamelaucium* hybrid.
Variety denomination: 'Moonlight Delight'.

BACKGROUND OF THE INVENTION

The present invention relates to a new and distinct cultivar of *Chamelaucium*, botanically of hybrid origin. The new cultivar will be referred to hereafter by its cultivar name, 'Moonlight Delight'. 'Moonlight Delight' is a new cultivar of waxflower, an evergreen shrub grown for use as a landscape plant and is particularly suited for cut flower use.

The Inventor discovered the new cultivar of *Chamelaucium* in August of 2004 as a naturally occurring branch mutation of *Chamelaucium* 'Stefan's Delight' (not patented) in a field plot at a nursery in Coorow, Australia.

Asexual propagation of the new cultivar was first accomplished by the Inventor by stem cuttings in Coorow, Australia in 2004. Asexual propagation by stem cuttings has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Moonlight Delight' as a unique cultivar of *Chamelaucium*.

1. 'Moonlight Delight' exhibits large clear white flowers with crimson centers, with the white color retained as the flower age.
2. 'Moonlight Delight' exhibits red flower buds.

3. 'Moonlight Delight' exhibits a long harvest period as a cut flower; can be cut during bud stage, 50% flower stage, and 80/90% flower stage.
4. 'Moonlight Delight' exhibits petals that overlap.
5. 'Moonlight Delight' exhibits calyxes with the free apex portion remaining mostly white.
6. 'Moonlight Delight' is early blooming.

The parent 'Moonlight Delight', 'Stefan's Delight', differs from 'Moonlight Delight' in having smaller flowers that are less clear white and turn pink with age and in having petals that do not overlap. 'Moonlight Delight' can also be compared to the cultivars 'Blondie' (U.S. Plant Pat. No. 9,966) and 'Laura Mae Pearl' (not patented). 'Blondie' is similar to 'Moonlight Delight' in blooming early in the season and in having white flowers, however 'Blondie' differs from 'Moonlight Delight' in having smaller flowers that are creamy white in color with a slight pink blush at times, in having petals that do not overlap, and in having red-purple flower buds. 'Laura Mae Pearl' is similar to 'Moonlight Delight' in having large white flowers, however 'Laura Mae Pearl' differs from 'Moonlight Delight' in blooming later, and in having flowers that are less clear white and in having petals that are not overlapping.

BRIEF DESCRIPTION OF THE DRAWING

The accompanying colored photographs illustrate the overall appearance and distinct characteristics of the new cultivar. The photographs were taken of a one year-old plant of the new cultivar as grown outdoors in a field in Coorow, Australia.

The photograph in FIG. 1 provides a close-up view of the flowers and flower buds of 'Moonlight Delight'.

Figure 1:
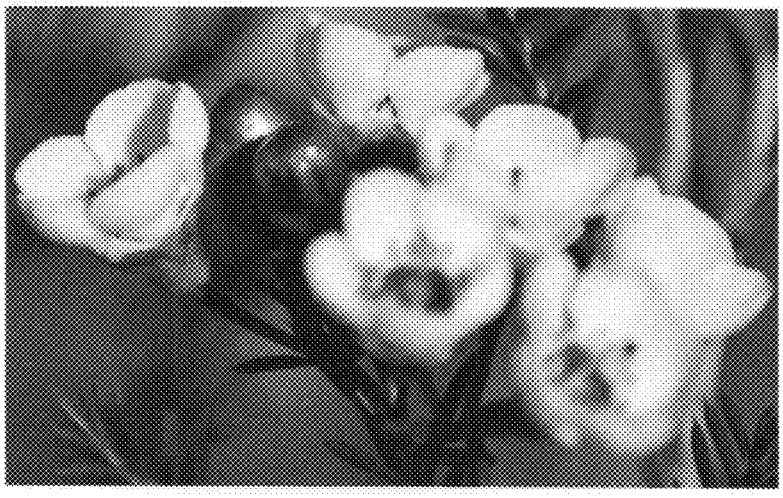
Figure 2:
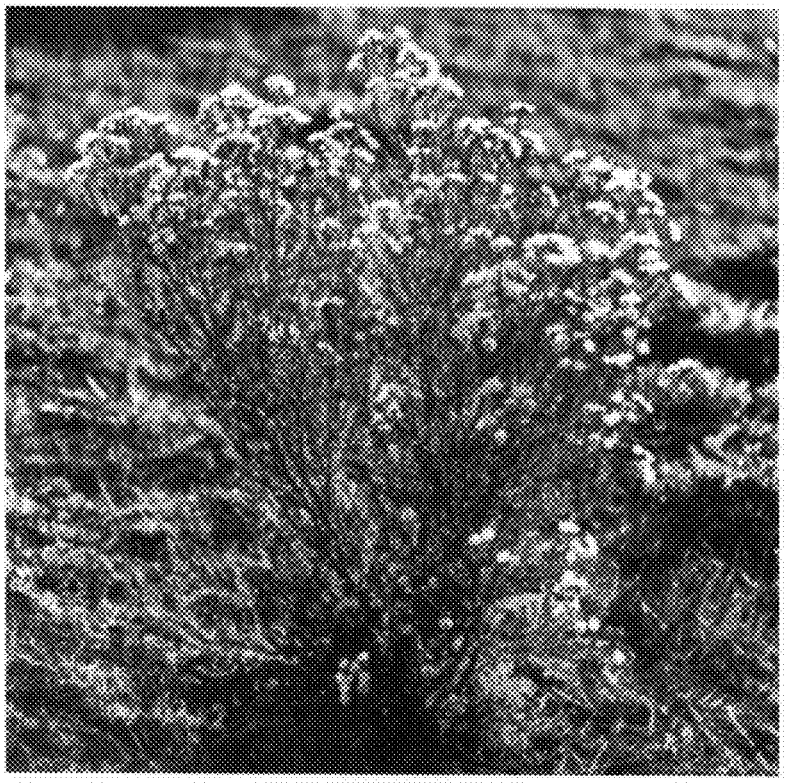

The photograph in FIG. 2 provides a view of the plant habit of 'Moonlight Delight'.

The colors in the photographs are as close as possible with digital photography techniques available, the color values cited in the detailed botanical description accurately describe the colors of the new *Chamelaucium*.

DETAILED BOTANICAL DESCRIPTION

The following is a detailed description of one year-old plants the new cultivar as grown outdoors in a field in Coorow, Australia. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Early blooming; blooms for 8 to 10 weeks in early to mid winter in Coorow, Australia.

*Plant type.*—Evergreen shrub.

*Plant habit.*—Upright and semi-open.

*Height and spread.*—1.5 m in height and 1.2 m in spread.

*Hardiness.*—At least in U.S.D.A. Zones 9 to 11.

*Diseases.*—No resistance or susceptibility to diseases has been observed.

*Environmental stresses.*—Grows well in sandy soil, low humidity and hot sun, tolerates mildly salty water.

*Propagation.*—Stem cuttings.

*Growth.*—Vigorous.

Branch description:

*Stem color.*—New growth; a blend of 162D and N167B, mature wood; a blend of 198A and 167A.

*Stem surface.*—New growth; slightly glossy and glabrous, mature wood; smooth and dull.

*Branching.*—Average of 4 basal branches, 10 lateral branches per basal branch, and 8 tertiary branches per lateral branch.

*Stem size.*—Basal branches; an average of 45 cm in length and 5 mm in width, lateral branches; an average of 30 cm in length and 4 cm in width, tertiary branches; an average of 8 cm in length and 1.5 mm in width.

Foliage description:

*Leaves.*—Simple, linear in shape, opposite arrangement, average of 1.3 cm in length and 2 mm in width, internode length up to 1 cm, attachment sessile, slightly glossy on both surfaces, color: new foliage all surfaces; 143A, base is 149B, mature foliage all surfaces; a blend of N137A and 137B with base is 151B.

Inflorescence description:

*Inflorescence type.*—Clusters on terminals and upper axils of main stems and lateral and tertiary branches.

*Inflorescence size.*—5 cm in length and 5 cm in diameter.

*Inflorescence number.*—Average of 9 per lateral branch.

*Flower number.*—Average of 7 per cluster (ranges from 2 to 12).

*Flower fragrance* .—Faint.

*Inflorescence longevity.*—About 5 weeks in the landscape.

*Longevity as a cut flower.*—7 to 12 days.

*Harvest production period for cut flowers.*—Up to 10 weeks; can be harvested at bud stage, 50% flower stage, and 80/90% flower stage.

*Harvest production yield.*—20 to 60 stems on a 2 year-old plant, 70 to 100 stems on plants 3 years old or more.

*Flower type.*—Cup shaped with base of corolla and fused to calyx.

*Flower size.*—Average of 1.2 cm in diameter and 1 cm in depth.

*Peduncles.*—Average of 1.2 cm in length and 1.5 mm in diameter, color a blend of 162D and N167B, surface is glabrous, smooth and satiny.

*Pedicels.*—Average of 1 cm in length and 1.5 mm in diameter, color 145A, surface is glabrous and satiny.

*Flower buds.*—Globose-obovate in shape, an average of 8 mm in length and 7 mm in width, color 155A and heavily suffused with 60A to 60B.

*Calyx.*—Campanulate and narrowing to tube (hypanthium), average of 1 cm in length and width including tube portion 4 mm in length and width.

*Sepals.*—5, fused with free apex an average of 2 mm in depth and 4 mm in width, margin entire, color of upper and lower surface 145A with free apex N155B occasionally suffused with 60C, both surfaces are glabrous and waxy.

*Petals.*—5, orbicular-obdeltoid in shape, slightly overlapping, slightly cupped, margin entire and slightly crenate on apex, base cuneate and fused to calyx and nectary, apex is rounded, average of 6 mm in length and 8 mm in width, color opening flowers upper and lower surface; NN155B with very slight markings of 60D, color 14 days after opening; 155B to 155C, surface glabrous and waxy on upper and lower surface.

*Nectaries* (*centers*).—Slightly cupped in shape, 1 cm in diameter and 3 mm in depth, 147B to 147C in color and suffused with 60B.

Reproductive organs:

*Pistils.*—1, stigma is an average of 1.5 mm in diameter, about 60D in color with hairs about 0.5 mm in length, style is an average of 5 cm in length and 1 mm in width (narrows at apex) and 155A in color, ovary is conical-shaped, 3 mm in length and width and 157D in color.

*Stamens.*—About 10, with 10 infertile stamenoids arranged between stamens, filaments are triangular in shape, up to 2 mm in length and 1.5 mm in width and 155A in color, anthers are an average of 0.5 mm in width and 162B in color, pollen not discernable, stamenoids; triangular in shape, average of 0.5 mm in length, 60C in color.

*Fruit and seed.*—Fruit production has not been observed to date.

It is claimed:

1. A new and distinct cultivar *Chamelaucium* plant named 'Moonlight Delight' as herein illustrated and described.

* * * * *